United States Patent [19]
Mischenko

[11] Patent Number: 5,295,972
[45] Date of Patent: Mar. 22, 1994

[54] HYPODERMIC SYRINGE WITH PROTECTIVE CAP

[75] Inventor: Peter S. Mischenko, Mount Prospect, Ill.

[73] Assignee: Metatech Corporation, Lake Forest, Ill.

[21] Appl. No.: 925,084

[22] Filed: Aug. 4, 1992

[51] Int. Cl.⁵ .............................................. A61M 5/00
[52] U.S. Cl. ..................... 604/192; 604/198; 604/263
[58] Field of Search ............... 604/110, 187, 192, 198, 604/263

[56] References Cited
U.S. PATENT DOCUMENTS

| | | | |
|---|---|---|---|
| 4,139,009 | 2/1979 | Alvarez | 604/198 |
| 4,795,432 | 1/1989 | Karczmer | 604/110 |
| 4,917,672 | 4/1990 | Terndrup et al. | 604/263 X |
| 4,998,922 | 3/1991 | Kuracina et al. | 604/192 |
| 5,013,305 | 5/1991 | Opie et al. | 604/198 X |
| 5,098,401 | 3/1992 | DeLange | 604/192 |

Primary Examiner—John D. Yasko
Attorney, Agent, or Firm—Jones, Day, Reavis & Pogue

[57] ABSTRACT

A device to protect against accidental exposure to the needle on a hypodermic syringe. A flexible tubular covering is attached to the syringe surrounding the needle and extending beyond the tip of the needle. A cap is mounted on the end of the tubular covering to enclose the needle tip. An orifice extends through the cap such that as the cap is retracted towards the syringe, the tubular covering is flexed allowing the needle to pass through the orifice in the cap.

2 Claims, 5 Drawing Sheets

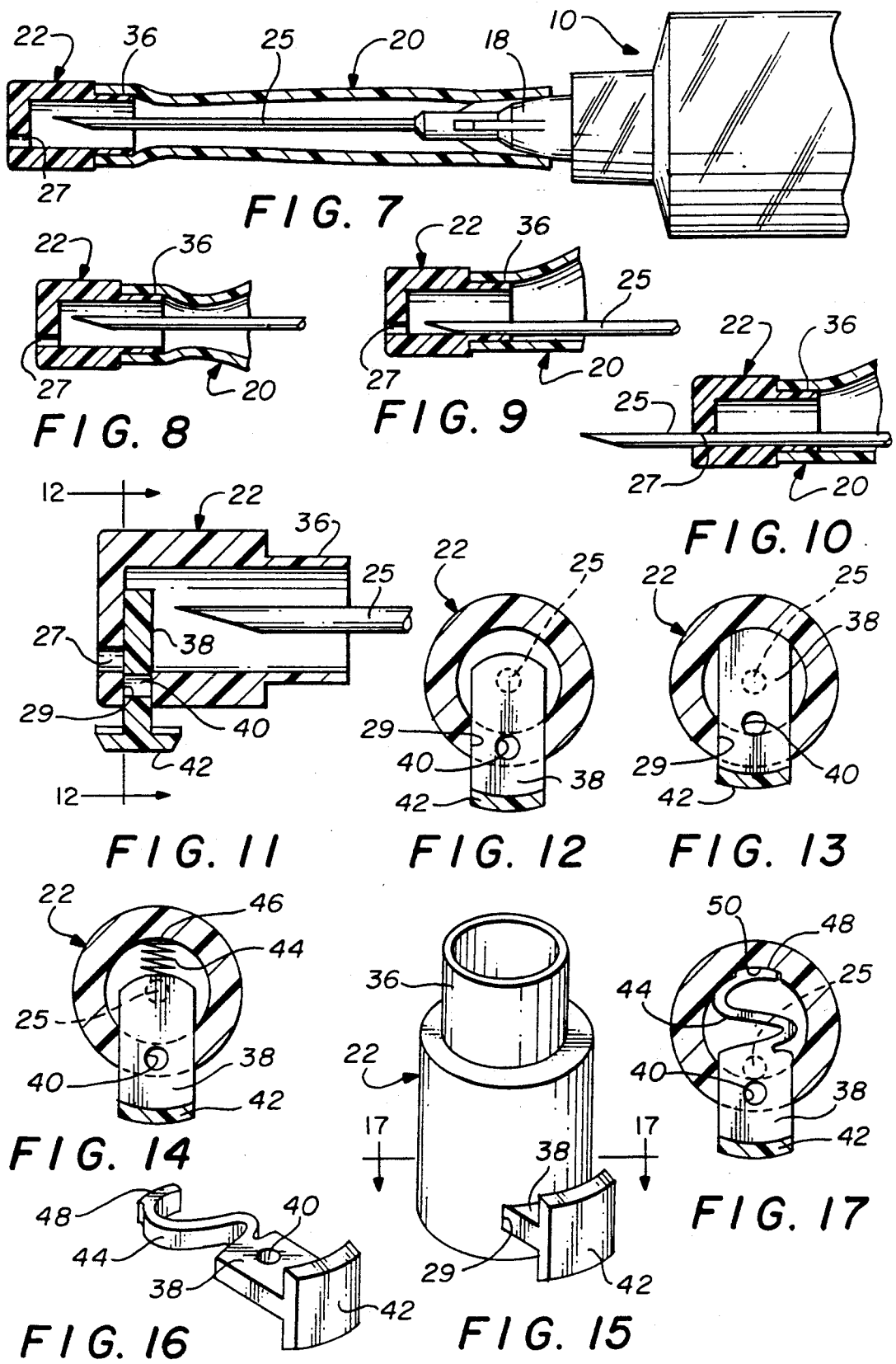

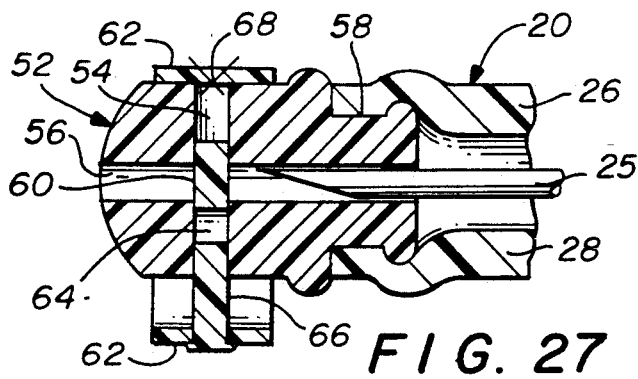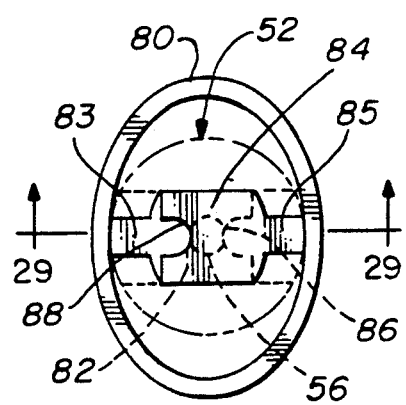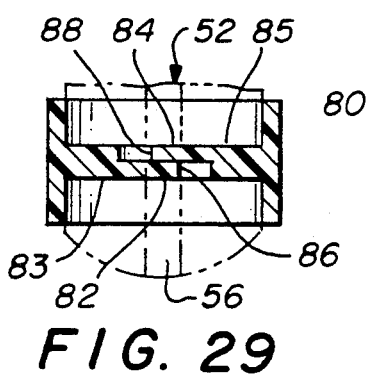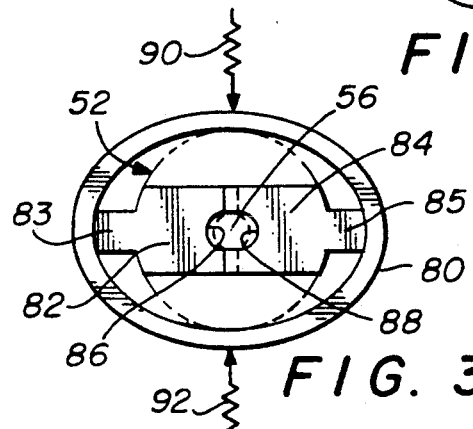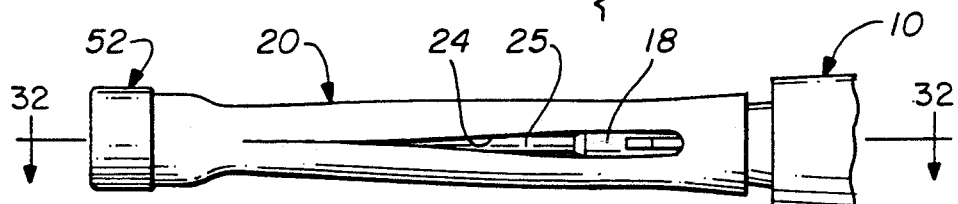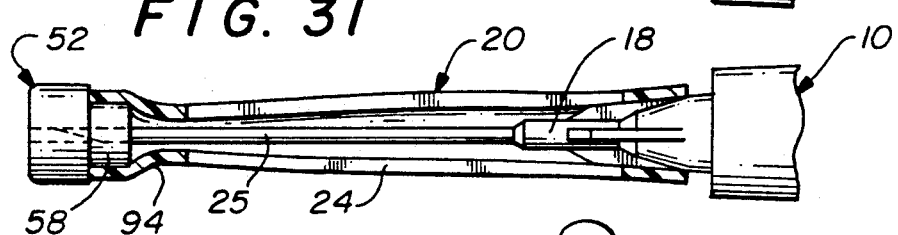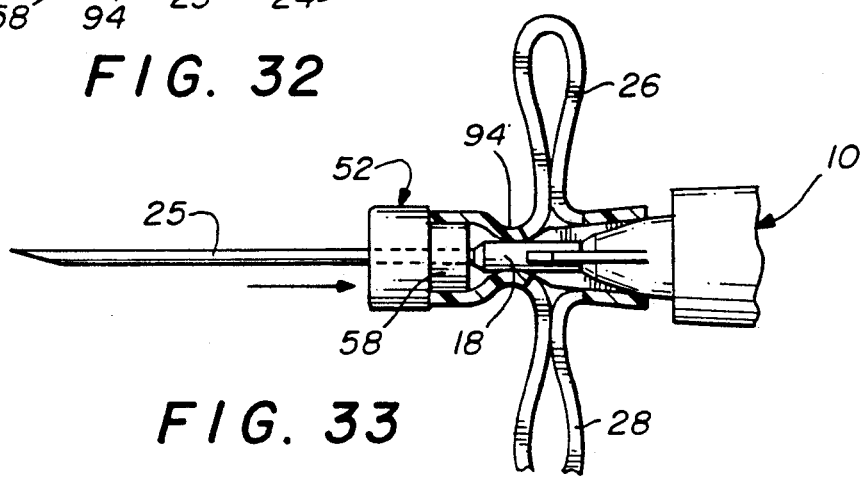

HYPODERMIC SYRINGE WITH PROTECTIVE CAP

FIELD OF THE INVENTION

The present invention relates in general to a device to protect against accidental exposure to syringe needles and in particular to a flexible covering surrounding the needle with a cap on the outer end thereof that encloses the needle tip and has an orifice therein such that, as the cap is retracted toward the spring, the tubular covering is flexed allowing the needle to pass through the orifice in the cap.

BACKGROUND OF THE INVENTION

A large number of injections of various liquids into the human body with a syringe having a needle thereon occurs each day in numerous locations including doctors' offices, hospitals, mobile intensive care units and the like. It is well known that in the process of giving an injection, the person giving the injection may accidentally come in contact with the exposed needle tip. This problem is of great significance today in view of the AIDS epidemic. It is important that a protector be provided that prevents accidental exposure to the needle. Such protection must be simple and easy to use and inexpensive to manufacture because of the large number that must be provided.

The present invention relates to a device to protect against accidental exposure to the needle on a hypodermic syringe. A flexible tubular covering made of silicone or other elastomeric material is attached to the syringe surrounding the needle and extends beyonds the tip of the needle. A cap is mounted on the end of the tubular covering to enclose the needle tip. An orifice extends through the cap such that as the cap is retracted toward the syringe, the tubular covering is flexed allowing the needle to pass through the orifice in the cap. In the preferred embodiment, at least two-spaced slits extend down the tubing from a point below the cap mounting to a point above the syringe attachment such that when the cap is pushed toward the syringe, the slit tube compresses outwardly on each side of the needle allowing the needle to pass through the cap orifice. The compressed tube acts as a spring and returns the cap over the needle tip after use of the needle. The cap is cylindrical in shape with a reduced diameter base for attachment of the elastomeric tubing and is open at only the end of the cap forming the reduced diameter base. The orifice is in the other closed end and in one embodiment is placed off center such that the cap must be deliberately pushed to one side to align the orifice with the needle thereby tending to prevent accidental exposure of the needle when the cap is inadvertently moved toward the syringe.

In another embodiment, a horizontal slot is formed in the side of the cap and a plate is slidably mounted in the cap slot for orthogonal movement with respect to the longitudinal axis of the cap. An orifice is positioned at one side of the plate such that the plate orifice is aligned with the cap orifice only when the plate is orthogonally moved with respect to the cap. This action enables the needle to pass through the aligned orifices when the cap is pushed toward the syringe. If desired, a resilient spring may be positioned between the cap and the slidable plate such that plate will be biased to a normal first position to cause the plate orifice to be out of alignment with the cap orifice to prevent accidental exposure of the needle if the cap is inadvertently moved toward the syringe and such that the plate may be forced to a second position aligning the plate orifice and cap orifice for enabling needle exposure and simultaneously compressing the resilient spring so that the plate will be returned to the normal first position when the force is removed.

In one embodiment, the plate is formed of molded plastic and the resilient spring is S-shaped and integrally formed at one end with the molded plastic plate. Further, a projection is integrally molded on the other end of the resilient spring and a recess is provided in the interior of the cap on the side opposite the slot such that the recess receives the projection on the resilient spring to hold the resilient spring in a stable position in alignment with the slot and the cap.

If desired, where the outer end of the syringe around the needle has a first diameter, the flexible tubular covering is utilized that has a second diameter sufficiently smaller than the first diameter such that the flexible covering can be forced over the first diameter of the syringe outer end to frictionally hold the cap in the retracted position during use of the needle and release it after use to return the cap to its normal position covering the needle tip.

If desired, the flexible tubular covering may be in the form of a bellows that, in a normal position, holds the outer end or cap covering the needle tip and, in a second position, when the bellows is compressed, allows the needle to pass through the orifice in the cap and the cap retracted. Again, where the outer end of the syringe around the needle has a first diameter, the bellows has a mating tubular end adjacent the cap with a second diameter sufficiently smaller than the first diameter of the outer end of the syringe such that the mating tubular end can be forced over the diameter of the syringe outer end to frictionally hold the cap in the retracted position during the use of the needle and be released after such use to return the cap to its normal position covering the needle tip.

The cap may have a solid body with a base for attachment to the flexible elastomeric tubing and an orifice extending longitudinally through the solid body of the cap. A molded horizontal slot may be formed in the cap extending at least partially through the solid cap orthogonal to the orifice. A plate is slidably mounted in the cap slot for orthogonal movement between first and second positions and an orifice is formed in the plate out of alignment with the cap orifice in the first plate position such that when the plate is moved to the second position, the plate orifice is in alignment with the cap orifice to enable the needle to pass through the aligned orifices when the cap is forced toward the syringe. The plate may have a resilient annular band eccentrically surrounding and attached to it on one side thereof to form a spring member movable between first and second positions. An elongated flat member serves as the plate and is attached at one end to the inside of the annular band with the other end inserted in the cap slot. The other side of the annular band is attached to the outside of the cap in alignment with the slot. The band, in such configuration, holds the plate in a first position. When the band is squeezed, the plate is forced inwardly in the slot to a second position. An orifice is formed in the flat member such that, in the first position of the band, the flat member orifice and the cap orifice are out of alignment and, in the second position of the band, the flat member orifice is in alignment with the cap orifice to allow the needle to pass therethrough when the cap is forced toward the syringe.

If desired, the resilient annular band may be formed in the shape of an oval that eccentrically surrounds the cap to form a spring member movable between first and second positions. A first elongated flat member serves as the plate and is attached at one end to a first position on the inside of the annular band on the minor axis of the oval and extends into the slot. A semicircular orifice is formed in the outer end thereof. A second elongated flat member is attached at one end to a second position on the inside of the annular band diametrically opposed to the first position on the minor axis of the oval and extends into the slot such that the outer ends of the two elongated members overlap. A second semicircular orifice is formed on the outer end of the second elongated flat member such that, in the normal first position of the oval shaped band, the two flat members overlap each other to prevent the needle tip from entering the cap orifice and when the oval shaped band surrounding the cap is compressed along the major axis, the outer ends of the first and second flat members move away from each other until the semicircles in the two members form a complete circle through which the needle can pass to the cap orifice.

Thus, it is an object of the present invention to provide a device that protects against accidental exposure to the needle on a hypodermic syringe.

It is also an object to the present invention to provide a protective covering surrounding the needle and attached to the syringe with a cap on the outer end thereof beyond and covering the needle tip and having an orifice in the cap such that when the cap is forced toward the syringe, the needle may pass through the orifice in the cap for use.

It is yet another object of the present invention to provide a resilient covering for a hypodermic needle that has a memory such that when the covering is compressed to expose the needle, it is automatically biased to cause it to return to its initial position covering the needle when it is released.

It is still another object of the present invention to provide a covering to protect against accidental exposure to a hypodermic needle, the covering having a cap on the outer end thereof that has an orifice through which the needle can pass. The covering is of such an inside diameter that it can frictionally adhere to the outer portion of the syringe below the needle to hold the cap in its retracted position until use of the needle is completed and then the compressed covering may be forcibly removed from its frictional engagement such that the compressed covering may return the cap to its initial position covering the needle tip.

It is also another object of the present invention to provide a bellows-type covering to protect against accidental exposure to a hypodermic needle, the bellows-type covering having a cap on the outer end thereof that has an orifice through which the needle can pass. The bellows has an outer end of such an inside diameter that it can frictionally adhere to the outer portion of the syringe holding the needle to hold the cap in its retracted position until use of the needle is completed and then the compressed bellows may be forcibly removed from its frictional engagement such that the bellows returns the cap to its initial position covering the needle tip.

SUMMARY OF THE INVENTION

Thus, the present invention relates to a device to protect against exposure to the needle on the hypodermic syringe comprising a flexible tubular covering attached to the syringe surrounding the needle and extending beyond the tip of the needle. A cap is mounted on the end of the tubular covering to enclose the needle tip. An orifice extends through the cap such that as the cap is retracted towards the syringe, the tubular covering is flexed allowing the needle to pass through the orifice and the cap. The flexible tubular covering may be an elastomeric tubing having at least two spaced slits extending down the tubing from a point below the cap to a point above the syringe attachment such that when the cap is pushed toward the syringe the slit tube compresses outwardly on each side of the needle allowing the needle to pass through the cap orifice. The compressed tube has a memory and returns the cap over the needle tip after use of the needle.

BRIEF DESCRIPTION OF THE DRAWINGS

These and other objects of the present invention will be more fully disclosed in the following detailed description of the accompanying drawings in which like numerals represent like elements and in which:

FIG. 7 is a cross-sectional view of a cap with an offset orifice and the flexible tubing mounted on the cap and on the syringe;

FIG. 8 is a partial cross-sectional view of the cap against the needle tip illustrating that if the cap is accidentally moved towards the needle, the needle is likely to impinge against the cap rather than the offset orifice;

FIG. 9 is a cross-sectional view of the outer end of the needle with the protective covering and cap illustrating how the cap has to be forced to one side to align the needle with the hole with the orifice in the cap;

FIG. 10 is a partial cross-sectional view of the outer end of the covering and cap illustrating the needle passing through the orifice in the cap;

FIG. 11 is a cross-sectional view of a modified cap using a movable plate having an orifice therein which, in a normal first position of the plate, blocks the cap orifice and in a second position of the plate aligns the plate orifice with the cap orifice to allow the needle to pass there through;

FIG. 12 is a cross-sectional view of the cap of FIG. 11 taken along lines 12—12 and illustrating the plate in its first position wherein the orifice in the plate is out of alignment with the orifice in the cap thus blocking the needle tip;

FIG. 13 illustrates the second position of the plate in FIG. 12 in which it is moved such that the orifice in the plate is in alignment with the offset orifice in the cap thereby enabling the needle to pass therethrough;

FIG. 14 is a cross-sectional view of an alternate embodiment of the cap of FIG. 11 in which a spring is formed between the plate and the cap to bias the plate into a first position in which its orifice is out of alignment with the orifice in the cap;

FIG. 15 is an isometric view of a cap having a slot therein with a plate slidably mounted therein such as in FIG. 11;

FIG. 16 is an isometric view of a plate having an orifice and a spring integrally molded with the plate for use with the cap of FIG. 15;

FIG. 17 is a cross-sectional view of a cap with the plate of FIG. 16 mounted therein;

FIG. 27 is a cross-sectional view of the flexible tubular covering and cap in its free state or normal position illustrating how the plate in the cap prevents the needle from being exposed;

FIG. 28 is a top view of an alternate embodiment of an oval shaped annular band having first and second plates therein that overlap to block the needle;

FIG. 29 is a cross-sectional view of the annular oval band and plate illustrated in FIG. 28 taken along lines 29—29;

FIG. 30 is a top view of the annular oval band of FIG. 28 illustrating that when the oval band is compressed along its major axis, the first and second plates separate to form an orifice through which the needle can pass;

FIG. 31 is a side view of the end of the syringe having the protector and cap thereon in its extended position;

FIG. 32 is a cross-sectional view of a portion of the cap and the protective tubing illustrating a tubing mating portion of the cap that is larger than the inside diameter of the tubing for frictional engagement therewith and the outer end of the syringe that also has a diameter larger than the tubing inside diameter;

FIG. 33 illustrates the syringe of FIG. 32 with the cap in its retracted position forcing the smaller inside diameter of the tube below the cap over the larger outside diameter of the outer end of the syringe such that friction of the tubing with the syringe out end holds the cap in its retracted position;

DETAILED DESCRIPTION OF THE DRAWINGS

Figure 1:
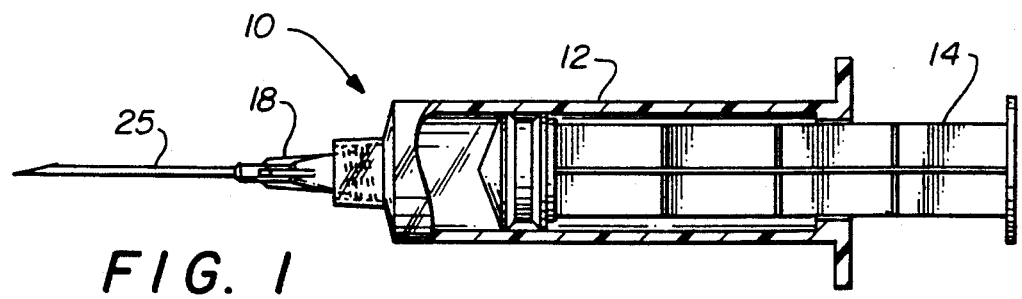
FIG. 1 is a diagrammatic representation of a hypodermic syringe with a needle.

FIG. 1 is a diagrammatic representation of a hypodermic syringe 10 having a hollow tube 12 with a plunger 14 therein and a needle 25 attached to the outer end 18 thereof. This is the type of syringe that can accidentally expose the needle to a user.

Figure 2:
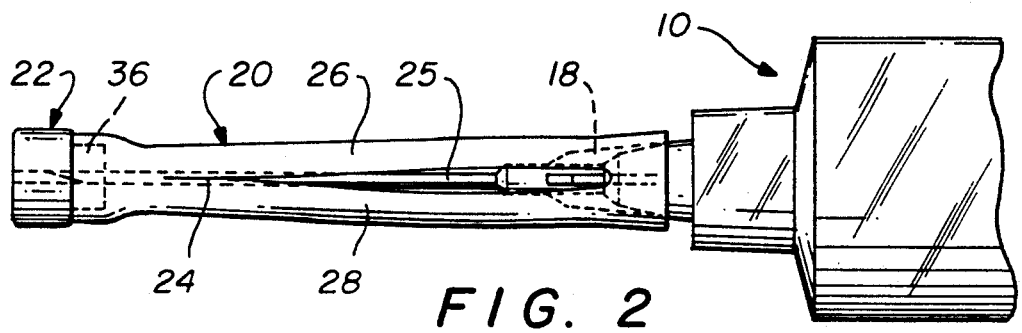
FIG. 2 is a diagrammatic representation of the present invention including a silicone or other elastomeric tubing covering the needle and having a cap with an orifice therein that extends beyond the tip of the needle; longitudinal slits partially divide the tube in at least two segments such that when the cap is forced toward the syringe with the orifice in alignment with the needle, the tubing can compress.

FIG. 2 is a side view of the outer end of a syringe 10 such as illustrated in FIG. 1 with a flexible tubular covering 20 attached at one end to the outer end 18 of the syringe and at the other end to a cap 22 that has an orifice therein through which the needle can pass as will be shown later in relation to FIGS. 4, 5 and 6. It will be noted that the covering 20 can be made of silicone or other elastomeric tubing. At least two slits 24 are formed in a portion of the tubing 20 that will divide the tubing into two or more segments when the cap 22 is forced towards the syringe 10.

Figure 3:
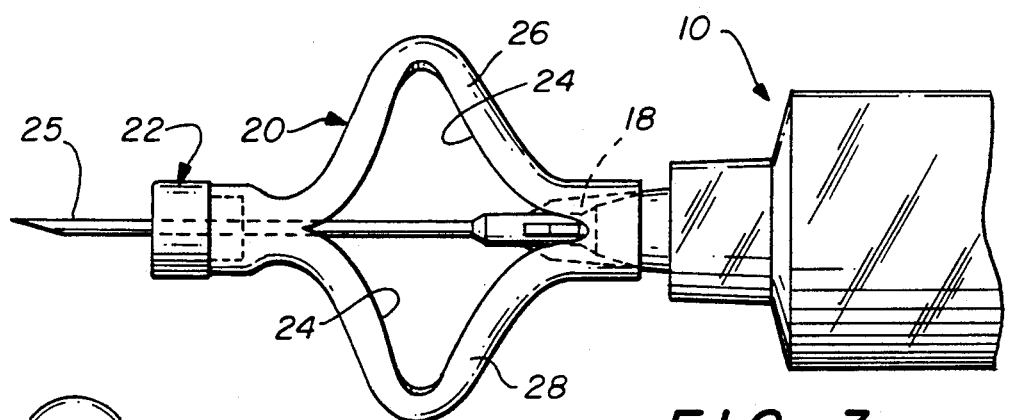
FIG. 3 is a diagrammatical representation of the outer end of the syringe with the cap having been pushed toward the syringe, the needle passing through the orifice and the tubing being compressed and acting as a spring.

FIG. 3 illustrates the cap 22 having been forced toward the syringe 10 thus causing the tubular covering 20 to be compressed into two segments 26 and 28 by diametrically opposed slits 24. Because the tube 20 has a memory when compressed as shown in FIG. 3, the tubing 20 acts as a spring and when the pressure is removed from the cap 22 the compressed tubing 20 returns the cap 22 to its normal position illustrated in FIG. 2 thus covering the end of the needle 25.

Figure 4:
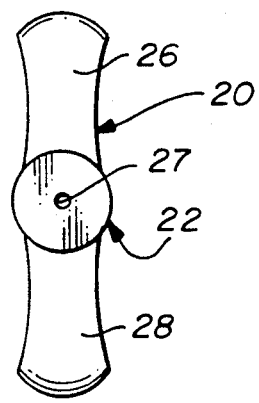
FIG. 4 is a top view of the syringe in FIG. 3 illustrating the cap and the tubing with two slits being compressed into two segments.

FIG. 4 is a top view of the syringe in FIG. 3 wherein the tubing 20 has been compressed to illustrate the two segments 26 and 28 extending on each side of the needle 25.

Figure 5:
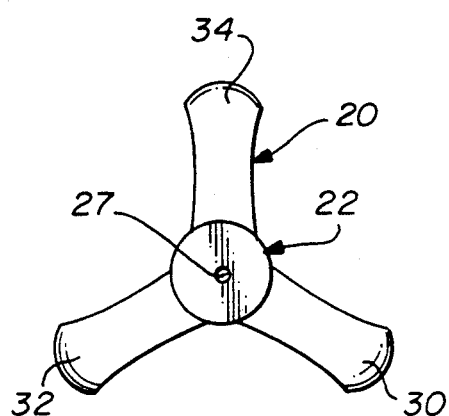
FIG. 5 is a top view of the syringe illustrating the tubing having been formed into three segments with three slits.

FIG. 5 illustrates the top view of the syringe in FIG. 3 if three equally spaced slits were made to form three segments 30, 32 and 34.

Figure 6:
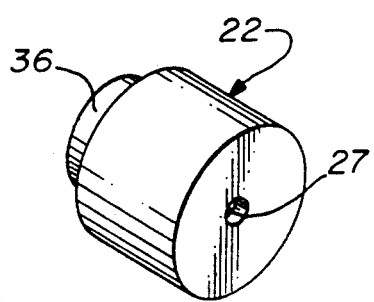
FIG. 6 is an isometric view of the cap with the orifice therein.

FIG. 6 is an isometric view of the cap 22 with orifice 27 therein. The cap 22 has a base 36 that has a slightly larger outside diameter than the inside diameter of the tubing 20 so that the flexible tubing 20 can be frictionally adhered to the base 36 of the cap 22.

FIG. 7 is a partial cross-sectional view of the cap and protective covering surrounding the needle 25 indicating that the orifice 27 and the cap 22 is offset from alignment with the needle 25 such that if the cap were accidentally pressed downwardly as illustrated in FIG. 8, the needle 25 would engage the cap body rather than the orifice 27. If the cap 22 is forced to one side as illustrated in FIG. 9, the needle 25 can be in alignment with the orifice 27. Then, by forcing the cap 22 towards the syringe, the needle 25 can pass through the orifice 27 as illustrated in FIG. 10. The problem with this embodiment is that there is a chance that inadvertent alignment could occur that could lead to accidental exposure of the needle and puncturing of the skin of an individual.

To prevent such inadvertent exposure, a cap as illustrated in cross section in FIG. 11 could be used. Cap 22 in FIG. 11 has the orifice 27 therein and a slot 29 in the side thereof through which a flat plate 38 is inserted. The plate 38 has an orifice 40 therein and a handle 42 which can be used to move the plate from a first position in which orifice 40 is out of alignment with the cap orifice 27 and to a second position where the plate orifice 40 is in alignment with the cap orifice 27. FIG. 12 is a cross-sectional view of FIG. 11 taken along lines 12—12 illustrating the plate 38 in its normal first position such that the orifice 40 is out of alignment with the orifice 27 in the cap. The needle 25 contacts the plate 38 and cannot inadvertently be inserted through the orifice 27 in the cap 22 since orifice 27 is covered by the plate 38. However, when the plate 38 is moved inwardly as illustrated in FIG. 13, the orifice 40 is in alignment with the orifice 27 in the cap 22 and the needle 25 can be inserted through the aligned orifices simply by forcing the cap 22 to one side as illustrated in FIG. 10.

In order to have the plate 38 be biased into its normal first position so that it always prevents alignment of the plate orifice 40 and the cap orifice 27 in its normal free state position, a spring bias can be applied to the plate 38 as illustrated in FIG. 14. Thus as can be seen in FIG. 14, a spring 44 is attached to the flat plate 38 at one end in any well-known manner and at the other end to the cap 22 at 46. Thus the spring biases the flat plate 38 in a first position such that the orifice 40 in plate 38 is out of alignment with the orifice 27 in the cap 22. The spring 44 may be of any well-known type so long as it biases the plate 38 into a normal free state position where the orifices 40 and 27 are nonaligned.

FIG. 15 is an isometric view of the cap 22 illustrating the plate 38 slidably mounted in the slot 29 and biased to its normal free state position. FIG. 16 illustrates the preferred embodiment of the plate 38 in which the spring 44 is integrally molded with the plate 38 in the shape of an S. The outer end of the S-shaped spring 44 has a projection 48 molded thereon for engagement with a recess 50 on the interior of the cap 22 on the side wall opposite the slot 29 as illustrated in FIG. 17. The recess 50 receives the projection 48 on the resilient spring 44 to hold the resilient spring 44 in a stable position in alignment with the slot 29 in the cap 22. Thus as can be seen in FIG. 17, the spring 44 biases the plate 38 to a first position where the orifice 40 in the plate 38 is not aligned with the orifice 27 in the cap. Thus, the needle 25 cannot be exposed unless the plate 38 is deliberately moved from its first position to its second position thus compressing spring 44. In the second position the orifices 40 and 27 are aligned and the needle can pass therethrough.

Figure 18:
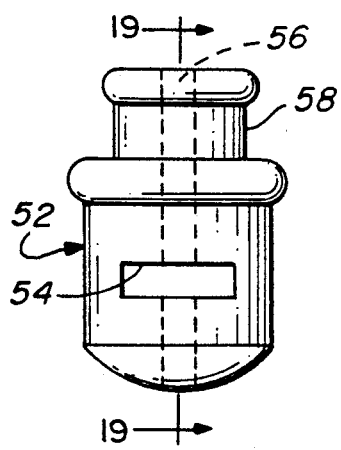
FIG. 18 is a cross-sectional view of a cap in the form of a solid body having a longitudinally extending orifice therein and a molded slot extending through the cap orthogonal to the orifice.
Figure 19:
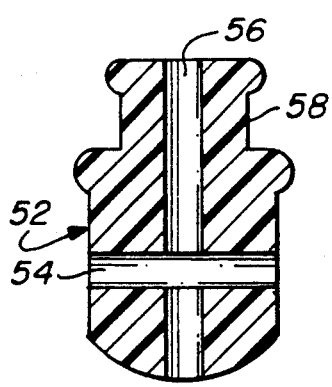
FIG. 19 is a cross-sectional view of the cap in FIG. 18 taken along lines 19—19.
Figure 20:
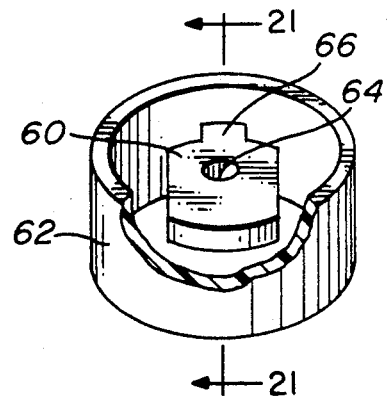
FIG. 20 is an isometric view of an alternate plate having an orifice therein with the plate being integrally formed with an annular collar that acts as a spring.
Figure 21:
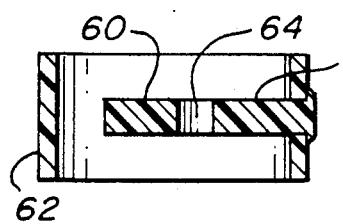
FIG. 21 is a cross-sectional view of the spring plate in FIG. 20 taken along line 21—21.
Figure 23:
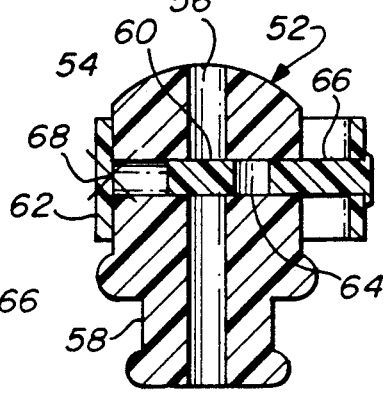
FIG. 23 is a cross-sectional view of the spring plate of FIG. 20 attached to a cap such that the plate is biased in a normal first position blocking the orifice in the cap.
Figure 24:
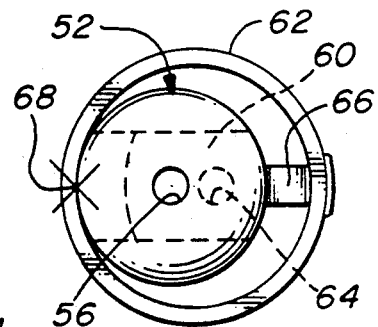
FIG. 24 is a top view of the cap in FIG. 23 illustrating the annular band being attached on one side of the cap and biasing the plate to its first position such that the plate orifice is not aligned with the cap orifice.
Figure 22:
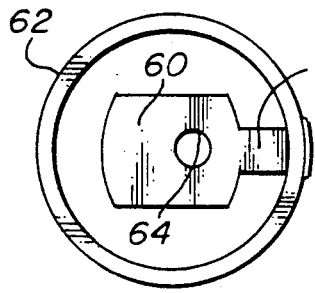
FIG. 22 is a top view of the spring plate illustrated in FIG. 20.
Figure 25:
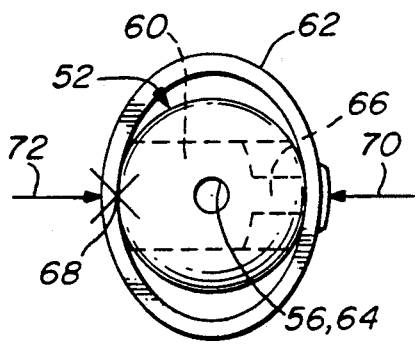
FIG. 25 is a top view of the cap in FIG. 23 illustrating the annular band being squeezed to force the plate to its second position in the slot aligning the orifice in the plate with the orifice in the cap.

As illustrated in FIG. 18, an alternate embodiment cap 52 is shown. The cap 52 has a solid body with a base 58 for attachment to the flexible elastomeric tubing 20 previously disclosed. An orifice 56 extends longitudinally through the solid body of the cap 52. A molded slot 54 extends at least partially through the solid cap 52 orthogonal to the orifice 56 and in the embodiment shown in FIG. 18 and FIG. 19, the slot 54 extends all the way through the solid body 52. A plate 60 as illustrated in FIG. 20 is provided for slidable mounting in the cap slot 54 for orthogonal movement between first and second positions. As indicated in FIG. 20, a resilient annular band 62 is formed for eccentrically surrounding and being attached to the cap 22 on one side thereof as illustrated in FIG. 23. In this position, the annular band 62 forms a spring member that can move the plate 60 between first and second positions. As illustrated in FIG. 20, the plate 60 has an orifice 64 therein and is attached at the end 66 to or integrally formed with the resilient annular band 62. FIG. 21 is a cross-sectional view of the annular band taken along lines 21—21 of FIG. 20. FIG. 22 is a top view of the resilient annular band 62 with the flat plate 60 therein having orifice 64. Thus, as stated earlier, in relation to FIG. 23, the elongated flat member 60 is attached at one end 66 to or integrally formed with the inside of the annular band 62 with the flat plate itself being inserted in the cap slot 54 shown in FIG. 18 and FIG. 19. The orifice 64 in the flat member 60 is positioned such that in the stable first position of the band 62 as illustrated in FIG. 23 the flat member orifice 64 and cap orifice 56 are out of alignment. This relationship is also illustrated in FIG. 24 which is a top view of the device in FIG. 23. Note that with the annular band 62 attached to the cap 52 at 68 in any well-known manner, the plate 60 is forced to the right in FIG. 24 by the annular band thus causing orifices 64 and 56 to be out of alignment. However, as illustrated in FIG. 25, when the annular ring 62 is depressed with the force being applied at point 66, the flat plate 60 moves inwardly through slot 54 thus causing orifice 64 to align with orifice 56 as illustrated in FIG. 25. Thus the force needs to be applied in the direction of arrows 70 and 72 in FIG. 25. When the force is released, the resilient nature of annular band 62 requires it to return to its original shape as illustrated in FIG. 24 thus forcing the plate 60 to the right as shown in FIG. 24 and moving the orifices 56 and 64 out of alignment to once again provide a protective cover for the needle to prevent accidental contact therewith.

Figure 26:
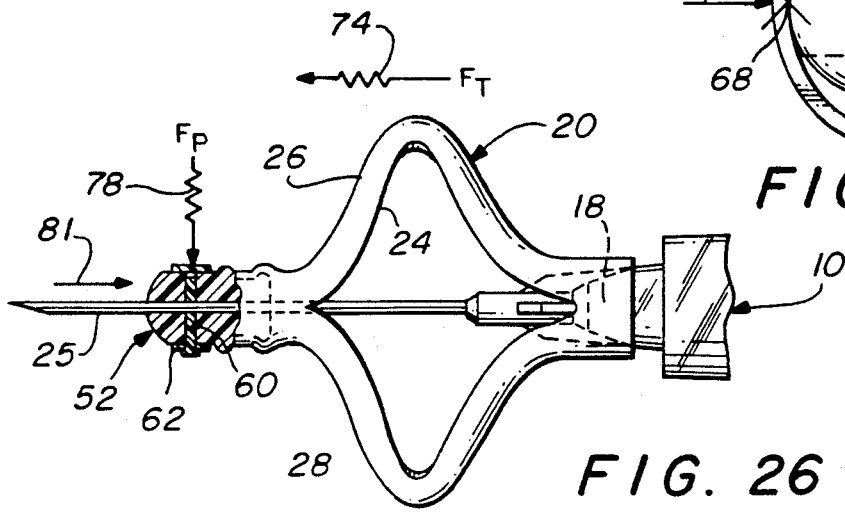
FIG. 26 is a diagrammatic representation of the tubular covering being recessed such that the needle of the syringe extends through the orifice in the cap and illustrates the forces existing in the flexible tubular covering and the plate spring.

In each of the cases previously discussed wherein a spring member is used to bias the plate to its normally nonaligned free state position, friction force, $F_f$ must be overcome by the spring force of the compressed tube in all positions along the needle. Thus as shown in FIG. 26, the frictional force $F_f$ designated by the arrow 80 that is generated by the plate spring force $F_p$ (designated by the numeral 78) against the needle 25 must be less than the spring force $F_t$, designated by the numeral 74, of the resilient spring formed by the compressed tube section 26 and 28 in all positions along the needle. This enables the force 74 of the tube spring to force the plate 60 to the free state position where the orifices are nonaligned beyond the tip of the needle thus preventing the needle from accidental exposure. FIG. 27 illustrates the needle in the free state position where the plate 60 blocks the orifice 56 of the cap 22 thus providing a protection against accidentally contacting the needle 25.

FIGS. 28, 29 and 30 illustrate another embodiment of a spring loaded plate. As illustrated in FIG. 28, the resilient oval shaped annular band 80 may concentric surround a cap 52 such as illustrated in FIG. 18 to form a spring member moveable between first and second positions. A first elongated flat member 82 is attached at one end 83 to a first position on the inside of the annular band 80 along the minor axis of the oval and extends into the slot 54 of the cap 52 as illustrated in FIG. 18. A semicircular orifice 86 is formed in the inner end of the first elongated flat member 82. A second elongated flat member 84 is attached at one end 85 to a second position on the inside of the annular band 80 diametrically opposed to the first position on the minor axis of the oval and extends into the slot 54 from the other side of the cap 52 such that the outer ends of the two elongated members 82 and 84 overlap as illustrated in FIGS. 28 and 29. A semicircular orifice 88 is formed in the inner end of the second elongated flat member 84 such that in the normal position of the oval shaped band 80, the two flat members 82 and 84 overlap to prevent the needle tip from entering the cap orifice 56. When the oval shaped band 80 is compressed along the major axis as illustrated by arrows and 90 and 92 in FIG. 30, the inner ends of the first and second flat members 82 and 84 move away from each other until the semicircles 86 and 88 in the two members 82 and 84 form a complete circle as illustrated in FIG. 30 through which the needle can pass through to the cap orifice 56.

Figure 34:
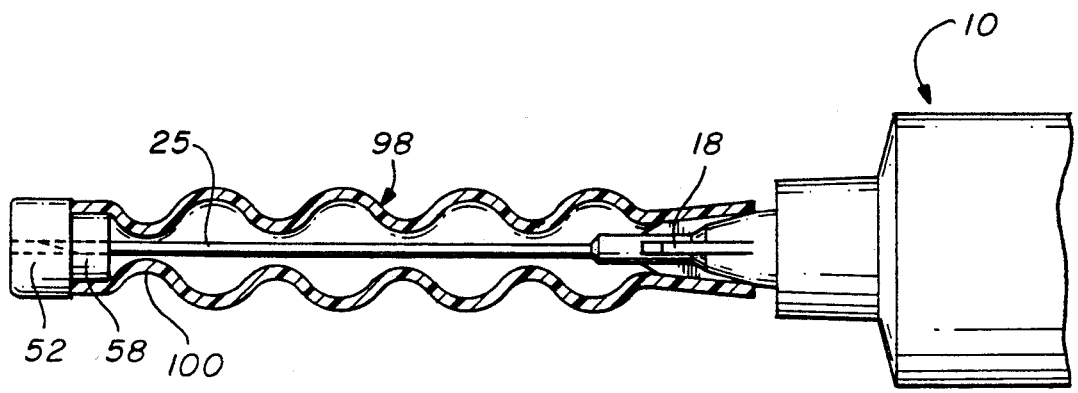
FIG. 34 is a cross-sectional view of a bellows-type covering surrounding the needle and preventing the needle from making accidental contact with a user.
Figure 35:
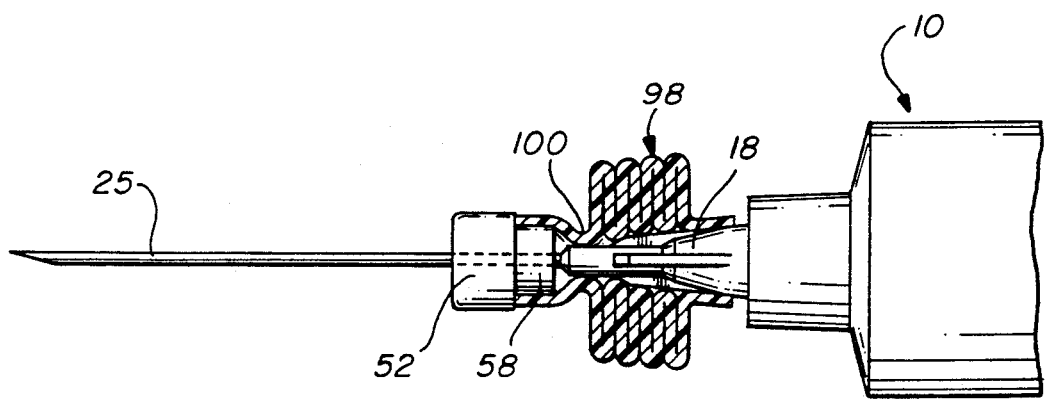
FIG. 35 is a partial cross-sectional view of the bellows-type arrangement of FIG. 34 with the bellows in its compressed state and illustrating the reduced diameter portion of the outer end of the bellows that frictionally adheres to the outer end of the syringe to hold the protective cap in a retracted position with the needle protruding therefrom for use.

FIG. 31 illustrates a side view of the end of a hypodermic needle 10 having any of the caps previously discussed on the end thereof and thus the cap in FIG. 18 designated by the numeral 52 will be shown. The tubing in 20 is attached to both the cap 52 and the outer end 18 of the syringe 10 surrounding the needle. FIG. 32 is a cross-sectional view of the tubing portion 20 illustrating means by which the protector cap 52 can be held in the retracted position while the needle 25 is being used. It will be noted in FIG. 32 that the mating diameter of base 58 of the cap 52 is larger than the inside diameter of the tube 20 thus providing a frictional engagement of the tube 20 with the cap 52. Note that the slit 24 begins at a point below the mating portion 58 of cap 52 and extends to a point beyond the outer cylindrical end 18 of the syringe 10 as shown in FIG. 32. Note also that a portion 94 of the tubing 20 below the cap 52 narrows as shown because its inside diameter is less than the outside diameter of the mating portion 58 of the cap 52. The slit 24 begins at a point below portion 94 of tubing 20. When the cap 52 is forced towards the syringe 10 as illustrated in FIG. 33, the narrow portion 94 of tube 20 is forced on and over the cylindrical end 18 of syringe 10. Because the cylindrical end 18 has a larger outside diameter than the inside diameter of the tube 20, the portion 94 of the tubing is held in frictional engagement with the cylindrical portion 18 of syringe 10. Friction holds the tube 20 and thus cap 52 in the retracted position. After use, pushing the cap 52 away from the syringe 10 towards the needle tip causes disengagement of the tubing portion 94 with the cylindrical portion 18 of the syringe thus enabling the spring pressure caused by compressed tube segments 26 and 28 to return the cap 52 to its protective position as illustrated in FIG. 31. FIG. 34 is a partial cross-sectional side view of still another embodiment of the present invention that utilizes a bellows 98 that is attached at one end to the syringe 10 and at the other end to a cap 52 which has the orifice for the needle 25 therein. In the position shown in FIG. 34, the bellows is extended and forces cap 52 beyond the end of needle 35 thus protecting the user from inadvertent contact with the needle 25. As shown in FIG. 35, when the needle is to be used, the bellows 98 is compressed, the needle 25 extends through the orifice in cap 58 and the reduced diameter portion 100 of the bellows 98 below cap 52 frictionally engages the outer shoulder 18 on the end of the syringe 10. The frictional engagement enables the bellows 98 to remain in the retracted position until the cap 52 is forcibly moved forward to remove the smaller diameter 100 of the bellows 98 from the shoulder 18 of syringe 10 thus allowing the bellows 98 to force the cap 50 to its original position beyond the end of needle 25 thus again shielding the user from inadvertent contact with the needle 25.

Thus there has been disclosed a novel device for protecting against accidental exposure to the needle on a hypodermic syringe. The novel device has a flexible tubular covering attached to the syringe and surrounding the needle and extends beyond the tip of the needle. A cap is mounted on the end of the tubular covering to enclose the needle tip. An orifice extends through the cap such that as the cap is retracted towards the syringe, the tubular covering is flexed thus allowing the needle to pass through the orifice in the cap. The tubing may be elastomeric and have at least two-spaced slits extending down the tubing from a point below the cap mounting to a point above the syringe attachment such that when the cap is pushed towards the syringe the tube segments formed by the slits compress outwardly on each side of the needle thus allowing the needle to pass through the cap orifice with the compressed tube forming a spring to return the cap over the needle tip after use. In one embodiment, the orifice in the cap is placed off center such that the cap must be deliberately pushed to one side to align the orifice with the needle thereby tending to prevent accidental exposure to the needle when the cap is inadvertently moved towards the syringe. In another embodiment, a slot is formed in the cap with a plate slidably mounted in the cap slot for orthogonal movement with respect to the longitudinal axis of the cap. The cap has an orifice and the plate has an orifice positioned such that only when the plate is orthogonally moved with respect to the cap orifice does the plate orifice align with the cap orifice so as to allow the needle to pass through the aligned orifices. A resilient spring may be positioned between the cap and the plate such that the plate will be biased to a first position to cause the plate orifice to be out of alignment with the cap orifice normally to prevent accidental exposure of the needle if the cap is advertently moved toward the syringe. The plate may be forced to a second position aligning the plate orifice and cap orifice to expose the needle while compressing the spring such that the plate will be returned to the first position by the compressed spring when the force is removed. Finally, the flexible tubing is designed such that it engages the outer end of the syringe and utilizes friction to hold the protective cap in the retracted position. After use, pushing the protector away from the syringe towards the needle tip causes disengagement and the cap is then forced into its protective position over the needle. The flexible tubing may be formed as a bellows arrangement that is designed such that at one end it engages the outer end of the syringe and the other end holds the protective cap. The bellows has a smaller diameter at the cap end than the outer end of the syringe. When the bellows is compressed the needle passes through the orifice in the end cap and the small diameter outer end of the bellows frictionally engages the outer end of the syringe and holds the protective cap in the retracted position.

Again, after use, pushing the protective cap away from the syringe toward the needle tip allows the bellows to return the cap to its initial position beyond the end of the needle, thus surrounding and shielding the needle so that it cannot accidentally contact an individual.

The foregoing specification describes only the embodiments of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

I claim:

1. A device to protect against accidental exposure to a needle on a hypodermic syringe comprising:
   a cap having a solid body with a base;
   a flexible, elastomeric tubular covering that extends beyond a tip of the needle to a front end that is attached to the cap base and extends to a back end that is attached to the syringe;
   an orifice extending longitudinally through the solid body of the cap;
   a molded slot extending through the solid cap orthogonal to the orifice;
   a resilient oval-shaped annular band surrounding the cap and forming a spring member movable between first and second positions;
   a first elongated, flat member attached at one end to a first position on an inside of the annular band along a minor axis of the oval-shaped band and extending into the slot;
   a semicircular orifice in an inner end of said flat member;
   a second elongated flat member attached at one end to a second position on the inside of the annular band diametrically opposite to the first position on the minor axis of the oval-shaped band and extending into the slot; and
   a semicircular orifice in an inner end of the second elongated flat member such that, in a normal position of the oval-shaped band, the two flat members overlap to prevent the needle tip from passing through the cap orifice, and when the oval-shaped band is compressed along a major axis, the inner ends of the first and second flat members move away from each other until the semicircles in the two members form a complete circle enabling passage of the needle through the cap orifice.

2. The device of claim 1, wherein the flexible elastomeric tubular covering comprises: at least two spaced slits extending down the tubular covering from a point below the front end to a point above the back end such that, when the cap is pushed toward the syringe, the slit tube compresses outwardly from the sides of the needle, allowing the needle to pass through the aligned orifices, the compressed tubular covering forming a spring for returning the cap to its position enclosing the needle tip after use of the needle.

* * * * *